(12) United States Patent
Kant

(10) Patent No.: US 6,248,908 B1
(45) Date of Patent: Jun. 19, 2001

(54) PROCESS FOR THE PREPARATION OF A PACLITAXEL C-4 METHYL CARBONATE ANALOG

(75) Inventor: Joydeep Kant, Cherry Hill, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/635,553

(22) Filed: Aug. 10, 2000

Related U.S. Application Data

(60) Provisional application No. 60/148,392, filed on Aug. 11, 1999.

(51) Int. Cl.[7] .................................................. C07D 305/14
(52) U.S. Cl. ............................................................... 549/510
(58) Field of Search ............................................. 549/510

(56) References Cited

U.S. PATENT DOCUMENTS

| | | |
|---|---|---|
| Re. 34,277 | 6/1993 | Denis et al. . |
| 5,274,124 | 12/1993 | Holton . |
| 6,025,385 * | 2/2000 | Shimizu et al. ........................ 514/449 |
| 6,147,234 * | 11/2000 | Holton et al. ........................ 549/510 |

FOREIGN PATENT DOCUMENTS

WO 94/14787    7/1994   (WO) .

OTHER PUBLICATIONS

Chen et al., J. Org. Chem., vol. 59, pp. 6156–6158 (1994).

Chen et al., Biorg. Med. Chem. Lett., vol. 5, No. 22, pp. 2741–2746 (1995).

* cited by examiner

*Primary Examiner*—Deborah C. Lambkin
*Assistant Examiner*—Sonya N. Wright
(74) *Attorney, Agent, or Firm*—Gabriel Lopez; Timothy J. Babcock

(57) ABSTRACT

A process for the synthesis of a C-4 methyl carbonate paclitaxel analog from 10-deacetylbaccatin III by the selective reduction of the acetate at the C-4 position of 10-deacetylbaccatin using Red-Al.

4 Claims, No Drawings

PROCESS FOR THE PREPARATION OF A PACLITAXEL C-4 METHYL CARBONATE ANALOG

RELATED APPLICATIONS

This application claims priority benefit under Title 35 § 119(e) of United States Provisional Application No. 60/148,392, filed Aug. 11, 1999, and entitled PROCESS FOR THE PREPARATION OF A PACLITAXEL C4 METHYL CARBONATE ANALOG, the entire contents of which are incorporated herein by reference.

BRIEF DESCRIPTION OF THE INVENTION

The present invention is directed to the synthesis of a paclitaxel C-4 methylcarbonate analog from 10-deacetylbaccatin III.

BACKGROUND AND SUMMARY OF THE INVENTION

The invention relates to the synthesis of C-4 methylcarbonate analog of paclitaxel having the formula

I

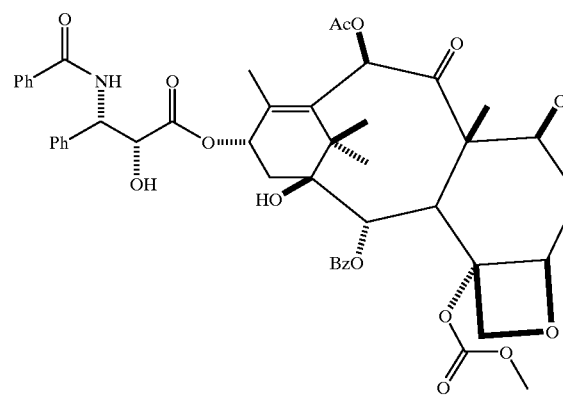

and intermediates useful for the preparation of novel antitumor agents starting from 10-desacetylbaccatin (10-DAB).

The compound of formula I is superior to paclitaxel in four distal site tumor models: M109 murine lung carcinoma; HCT/pk human colon carcinoma xenograft (multidrug resistant tumor model); L2987 human lung carcinoma xenograft; and HOC79, a clinically derived Taxol® unresponsive ovarian carcinoma xenograft. In the tubulin polymerization assay, compound I is about twice as potent as paclitaxel. Crystals of the compound of formula I display moderately increased solubility relative to paclitaxel in typical taxane vehicles and thus offers the potential for administration of less cremophor per dose than that currently administered with paclitaxel.

Previously, the original synthesis of the C-4 methyl carbonate analog of paclitaxel (I) required protections of C-2' and C-7 hydroxyl groups as silyl ethers; hydrolysis of C-2 benzoate and C-4 acetate; protection of C-1 and C-2 hydroxyl groups as cyclic carbonate; formation of C-4 methylcarbonate; regioselective opening of the carbonate to install C-2 benzoate; and removal of protecting groups to prepare I as indicated in Scheme 1.

Scheme 1 (Prior Art)-Synthesis of I from Paclitaxel

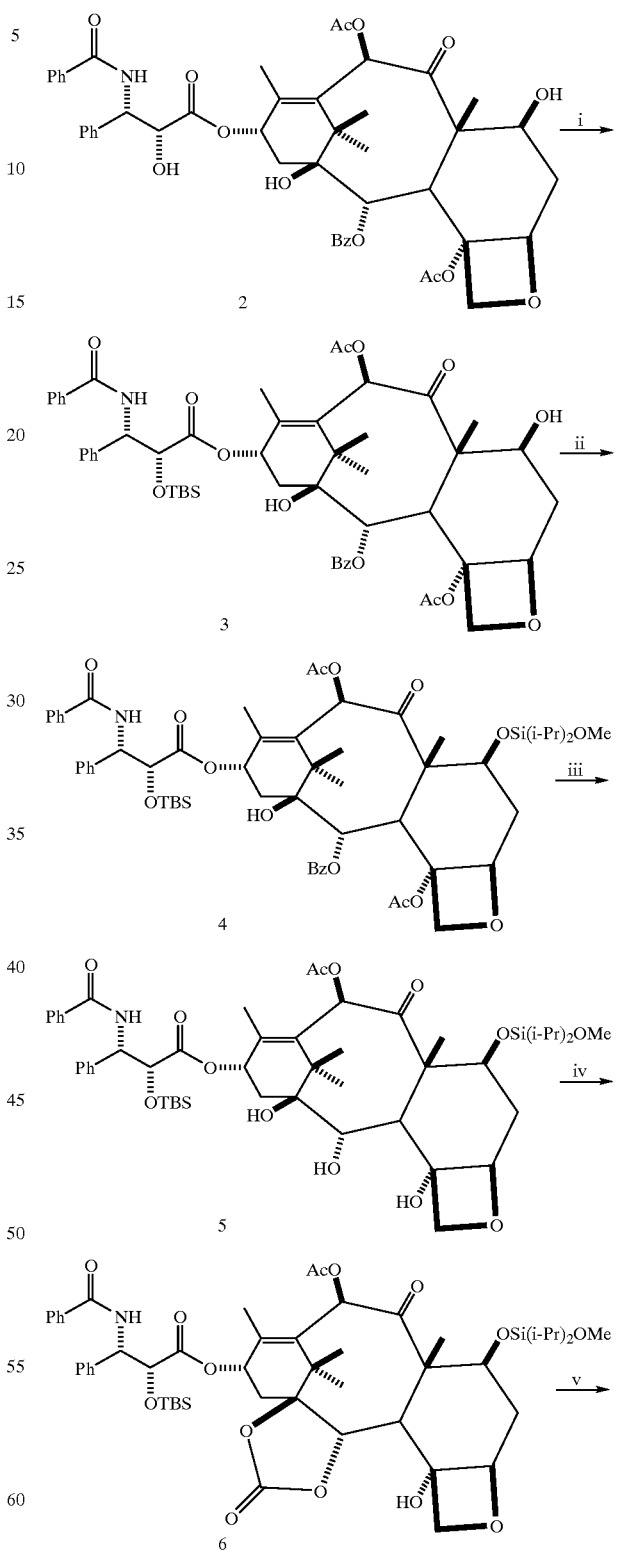

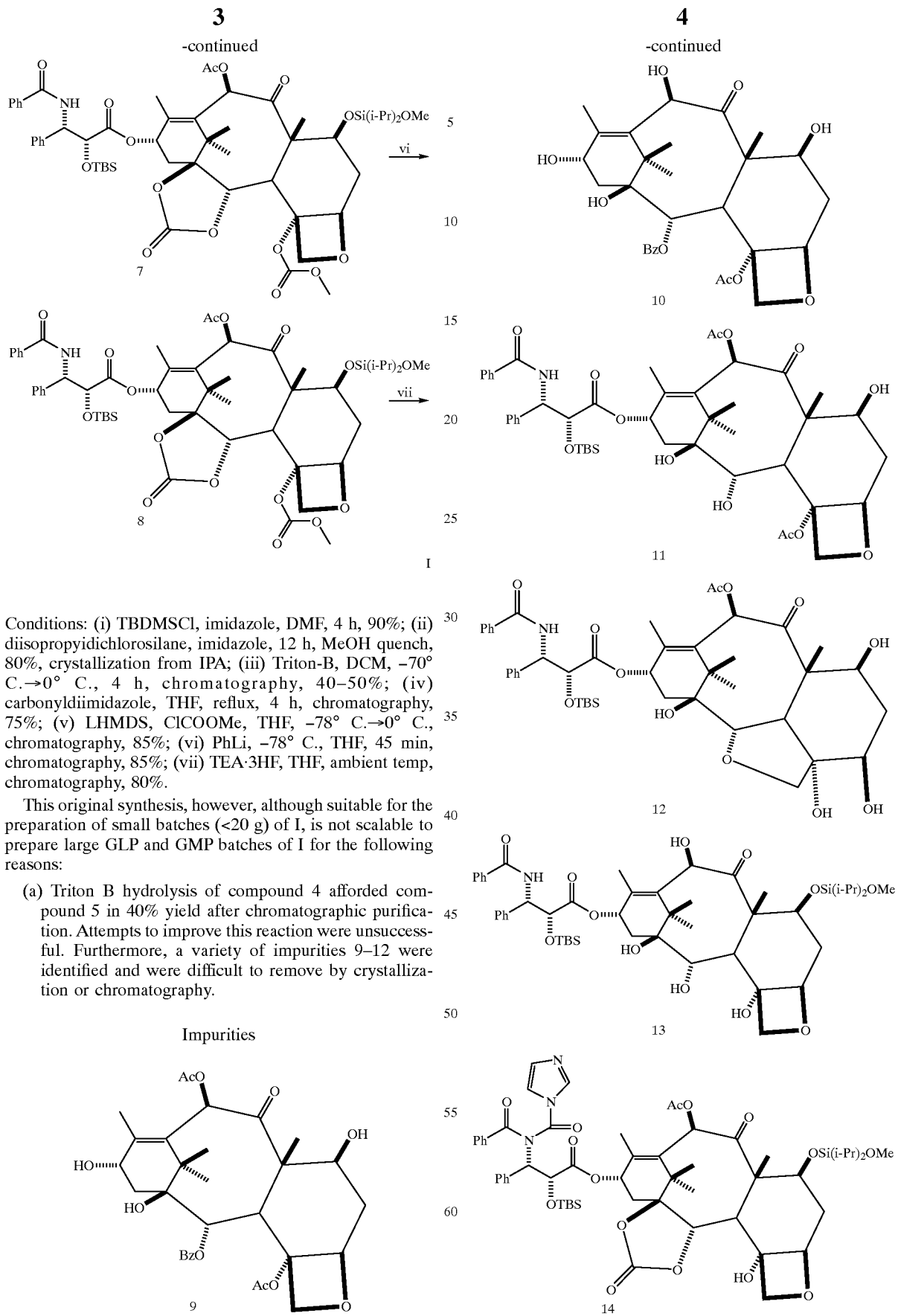

Conditions: (i) TBDMSCl, imidazole, DMF, 4 h, 90%; (ii) diisopropyldichlorosilane, imidazole, 12 h, MeOH quench, 80%, crystallization from IPA; (iii) Triton-B, DCM, −70° C.→0° C., 4 h, chromatography, 40–50%; (iv) carbonyldiimidazole, THF, reflux, 4 h, chromatography, 75%; (v) LHMDS, ClCOOMe, THF, −78° C.→0° C., chromatography, 85%; (vi) PhLi, −78° C., THF, 45 min, chromatography, 85%; (vii) TEA·3HF, THF, ambient temp, chromatography, 80%.

This original synthesis, however, although suitable for the preparation of small batches (<20 g) of I, is not scalable to prepare large GLP and GMP batches of I for the following reasons:

(a) Triton B hydrolysis of compound 4 afforded compound 5 in 40% yield after chromatographic purification. Attempts to improve this reaction were unsuccessful. Furthermore, a variety of impurities 9–12 were identified and were difficult to remove by crystallization or chromatography.

Impurities

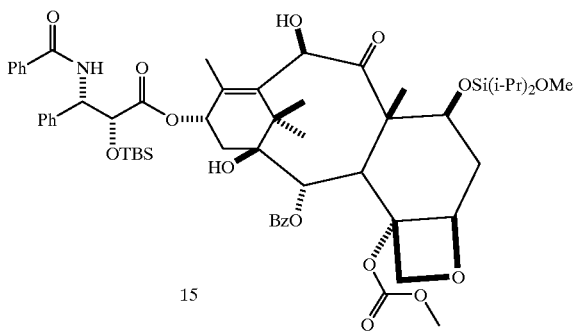

(b) Synthesis of the cyclic carbonate of compound 6 generated 5–10% of an N-acyl impurity 14 which was difficult to remove by crystallization.

(c) Treatment of phenyllithium with compound 7 produced approximately 10% of C-10 deacetate 15. The compound co-crystallized with the product.

(d) Purification of most of the intermediates required the additional step of column chromatography.

Synthetic routes for the preparation of compound I have been previously disclosed. See WO94/14787; Chen et al., "First Synthesis of Novel Paclitaxel (Taxol) Analogs Modified at the C4-Position", J. Org. Chem. 59 (21). pp. 6156–6158 (1994); Chen et al., "Novel C-4 Paclitaxel (Taxol®) Analogs: Potent Antitumor Agents", Bioorg. Med. Chem. Lett. 5 (22), pp. 2471–2476 (1995). However, none of these processes disclose the preparation of the compound of formula I starting from 10-DAB. Furthermore, the synthesis of the present invention provides a process wherein the acetate group at the C-4 position of 10-DAB is reductively removed using Red-Al prior to C-10 acetylation. As such, C-10 deacetylation side products are avoided.

DETAILED DESCRIPTION OF THE PRESENT INVENTION

In an effort to overcome these disadvantages, a more expedient synthesis of I was developed. This novel synthesis provides for the synthesis of I from readily available paclitaxel precursor 10-deacetylbaccatin ("10-DAB") 16 and is described in detail in Scheme 2.

In this novel process, the C-4 carbonate analog of 10-DAB 21 is viewed as the key intermediate in the synthesis of I. The key reaction in this novel synthesis is the chemoselective reduction of the C-4 acetate using Red-Al. The paclitaxel phenylisoserine side chain at C-13 is appended via the β-lactam route or oxazole based coupling chemistry, described in U.S. Pat. No. 5,274,124 (Holton) and U.S. patent application Ser. No. 07/995,443 respectively, and incorporated herein by reference, to provide the compound of formula I.

Scheme 2
Synthesis of I from 10-DAB

Step I: Protection of C-7, C-10, and C-13 hydroxyl groups as diisopropylmethoxysilyl ethers

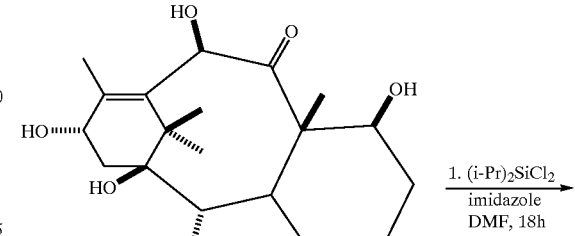

Step II: Protection of C-1 hydroxyl group as dimethylsilyl ether

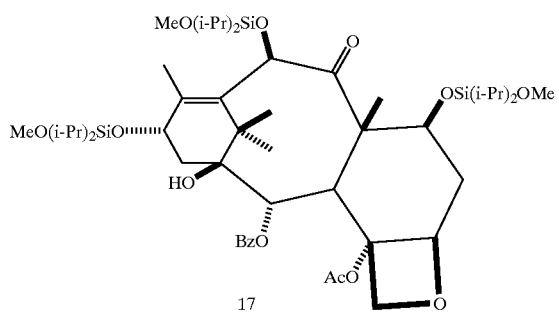

-continued
Step III. Reductive removal of C-4 acetate
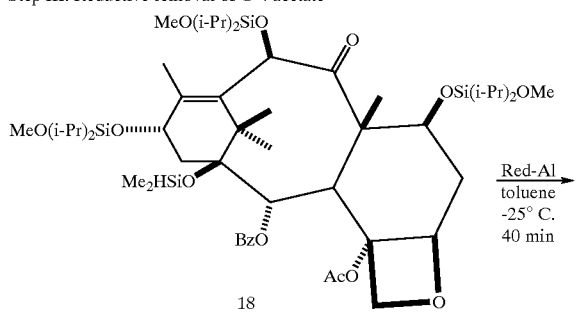
18
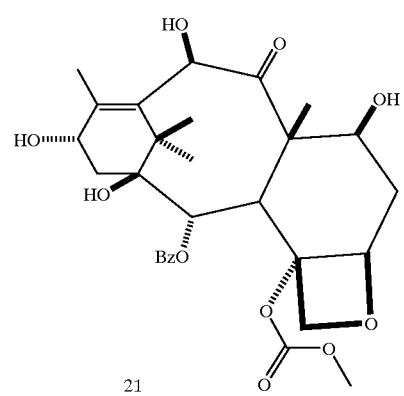
21
Step VI. Selective protection of C-7 hydroxyl as silyl ether
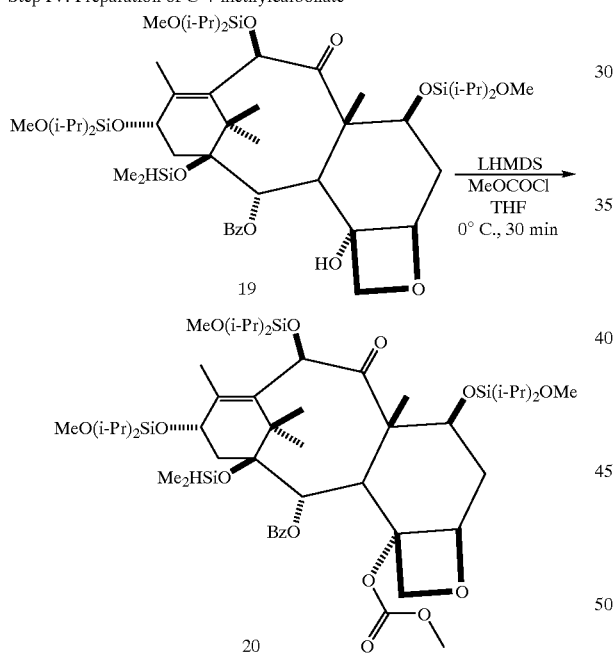
Step IV. Preparation of C-4-methylcarbonate
19
20
Step V. Deprotection of silyl ethers
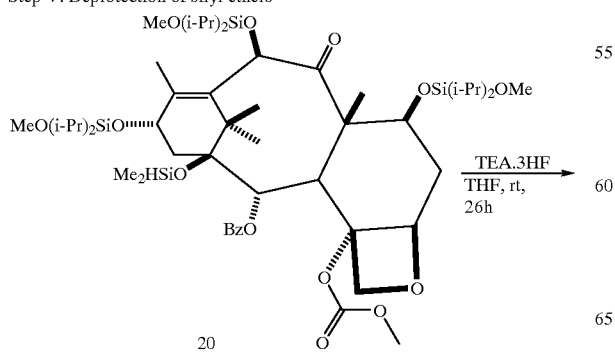
20
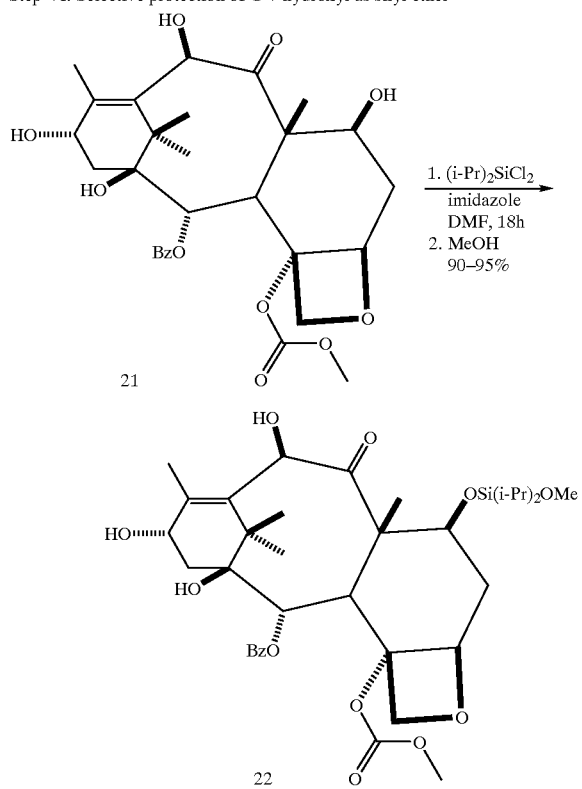
21
22
Step VIII. Coupling reaction to append the side chain
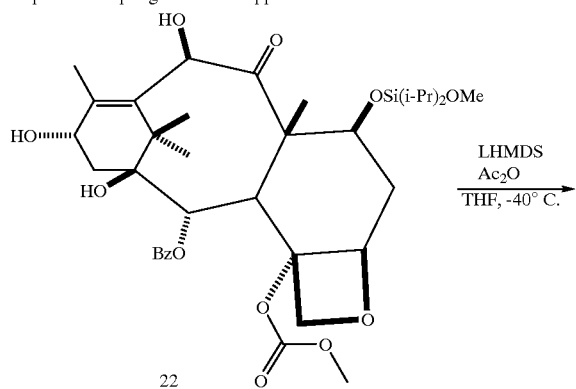
22

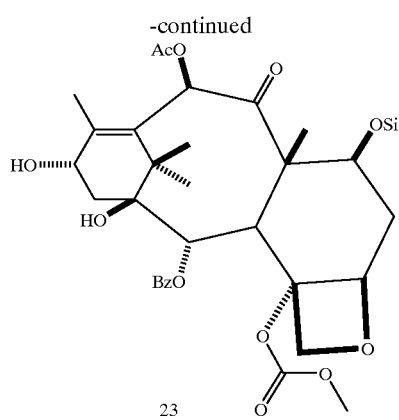

Step IX. Final deprotection preparation of I

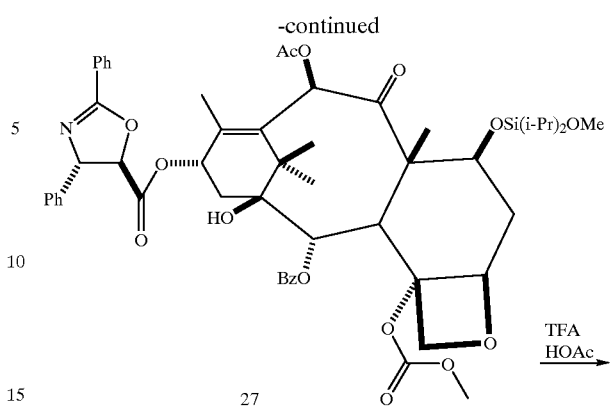

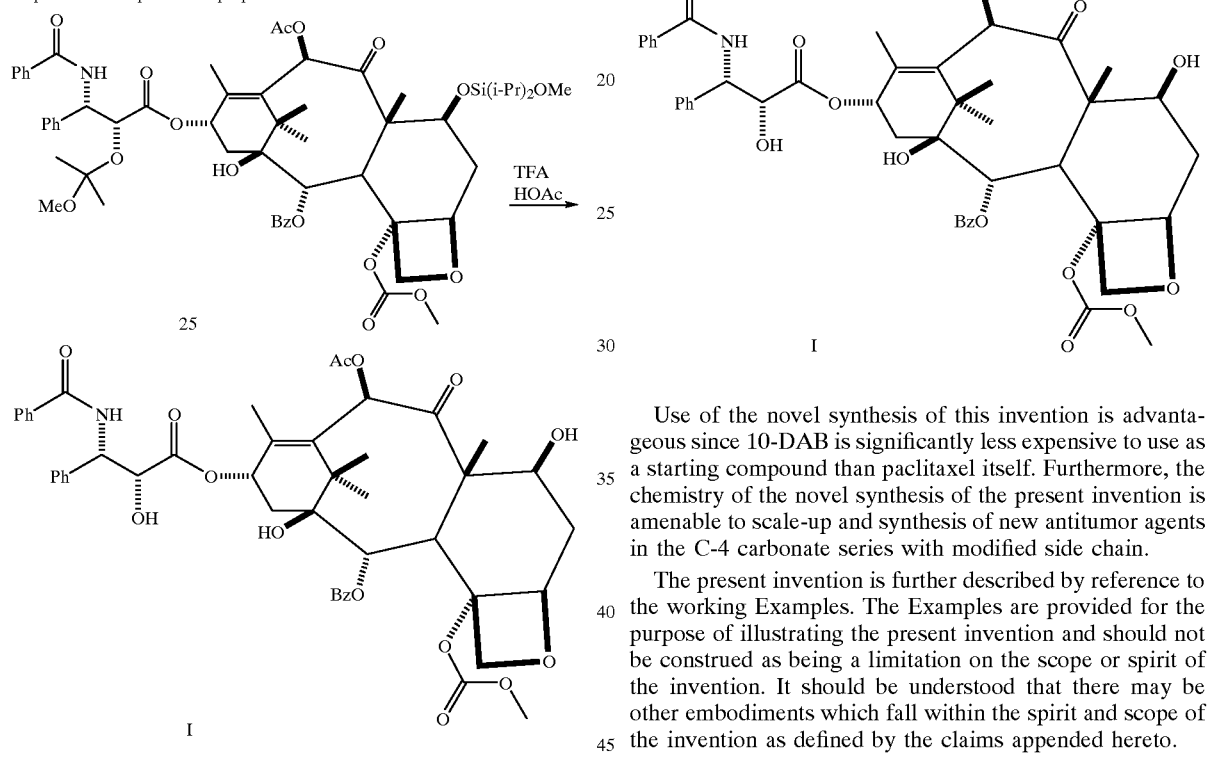

Alternate coupling via oxazole acid and its conversion to I

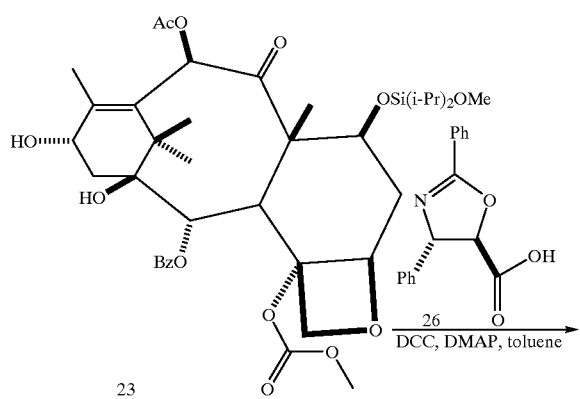

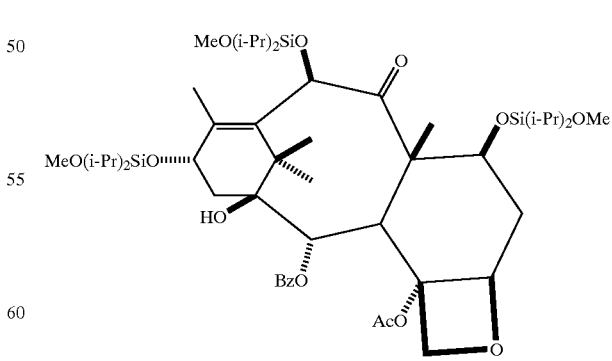

Use of the novel synthesis of this invention is advantageous since 10-DAB is significantly less expensive to use as a starting compound than paclitaxel itself. Furthermore, the chemistry of the novel synthesis of the present invention is amenable to scale-up and synthesis of new antitumor agents in the C-4 carbonate series with modified side chain.

The present invention is further described by reference to the working Examples. The Examples are provided for the purpose of illustrating the present invention and should not be construed as being a limitation on the scope or spirit of the invention. It should be understood that there may be other embodiments which fall within the spirit and scope of the invention as defined by the claims appended hereto.

EXAMPLES (1) Synthesis of baccatin derivative 17

To a solution of 10-desacetylbaccatin (16) (47.4 g, 87 mmol) in anhydrous N,N-dimethylformamide (DMF) (500 mL) was added imidazole (47 g, 691 mmol) at ambient temperature. Solution was stirred for 10–15 min until a clear solution was observed. Dropwise, diisopropyldichlorosilane (58 mL, 322 mmol) was added to the reaction mixture. Reaction mixture was stirred for 16 h at ambient temperature. Additional amount of diisopropyldichlorosilane (6 mL) was added to the solution and the reaction was stirred for 60 min. HPLC at this point indicated completion of the reaction. Methanol (36 mL) was added to the mixture and the solution was stirred for 60 min. Reaction was stopped and diluted with a mixture of tert-butyl methyl ketone (TBME) (500 mL) and water (200 mL). Layers were separated and organic phase was washed with brine (250 mL), dried (sodium sulfate) and evaporated to afford 17 (91 g, >100% yield) as a white amorphous compound which was used in the next step without further purification.

ESILRMS M+ calcd. For $C_{50}H_{84}O_{13}Si_3$: 977. Found 977

2) Synthesis of baccatin derivative 18

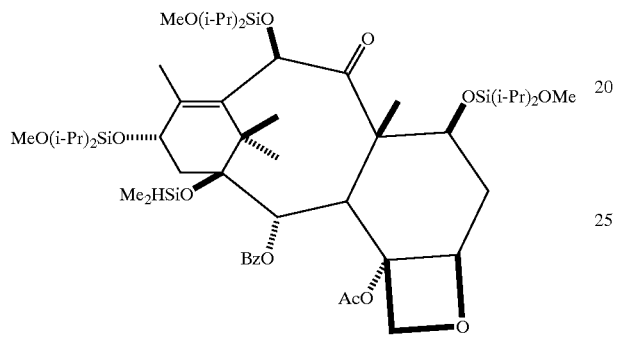

To a solution of baccatin derivative 17 (90 g, 92 mmol) in DMF (500 mL) was added imidazole (22 g, 320 mmol) at 0° C. Dimethylchlorosilane (35 mL, 320 mmol) was added dropwise at 0° C. Precipitation of the compound was observed at this point. Reaction mixture (slurry) was stirred for 0.5 h at 0° C. Solid was filtered and washed with cold DMF (3×150 mL). After air drying, solid was redissolved in TBME (700 mL) and the solution was washed with water (3×200 mL), brine (250 mL) and dried (sodium sulfate). The solution was filtered through a short silica pad. Removal of the solvent under vacuum afforded 18 in 77% yield (70 g).

ESILRMS M+ calcd. For $C_{50}H_{90}O_{13}Si_4$: 1035. Found 1035

3) Synthesis of baccatin derivative 19

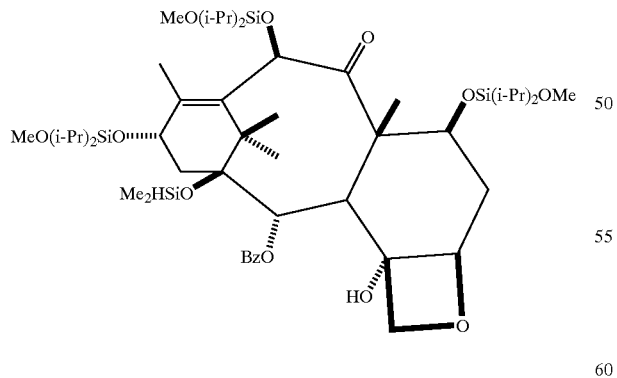

To a stirred solution of 18 (66.3 g, 64 mmol) in toluene (680 mL) at −34° C. was added Red-Al (50 mL, 160 mmol, 65 wt % solution of sodium bis(2-methoxyethoxy)aluminum hydride in toluene) dropwise over a period of 10 min. Reaction mixture was warmed to −25° C. and stirred for 1.5 h. Methanol (62 mL) was added dropwise to the reaction mixture keeping internal temperature between −20 and −25° C. Solution was diluted with TBME (500 mL) followed by the addition of 1N sodium hydroxide solution (60 mL) and brine (60 mL). Solution was stirred for 30 min. Celite (12 g) was added to the mixture, stirred for 10 min, and filtered through a pad of celite. Layers were separated. Organic layer was washed with water, brine, and dried (sodium sulfate). Next, solution was passed through a short silica pad before removal of the solvent. The compound was obtained in 97% yield (62 g) as a white solid.

ESILRMS M+ calcd. For $C_{50}H_{88}O_{12}Si_4$: 993. Found 993

4) Synthesis of baccatin derivative 20

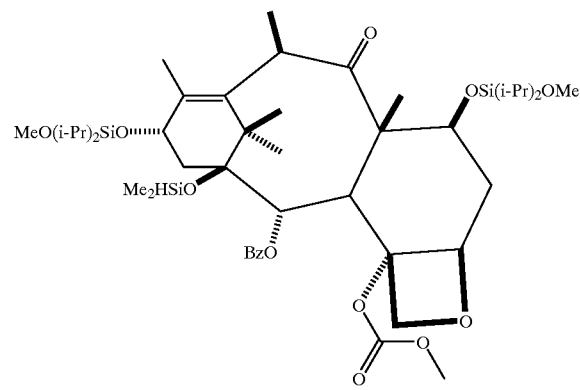

Under argon atmosphere, to a solution of 19 (62 g, 62 mmol) in anhydrous tetrahydrofuran (THF) (600 mL) at −60° C. was added LHMDS (lithium bis(trimethylsilyl) amide (125 mL, 125 mmol, 1M solution in THF) dropwise. Solution was stirred for 15 min followed by the addition of methyl chloroformate (9 mL, 116 mmol); internal temperature of the solution was maintained at −60° C. Reaction was slowly warmed to 0° C. and mixture was stirred for 3 h. After completion of the reaction, saturated ammonium chloride (300 mL) was added. Reaction mixture was extracted with TBME (100 mL). Organic layer was washed with saturated ammonium chloride (200 mL), water (200 mL), brine (200 mL), dried (sodium sulfate), and evaporated to provide 20 as an oil (67 g, >100%). The crude material was used in the next step without further purification.

ESILRMS M+ calcd. For $C_{52}H_{90}O_{14}Si_4$: 1051. Found 1051.

5) Synthesis of baccatin derivative 21

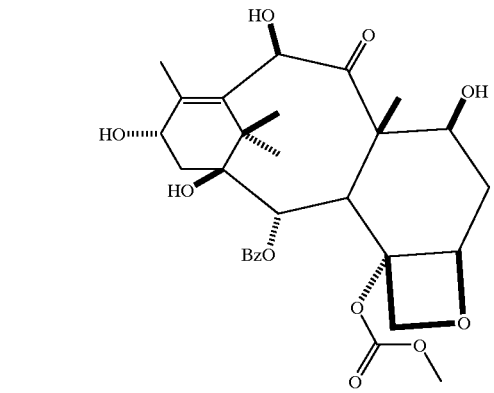

To a solution of baccatin derivative 20 (62 g, 59 mmol) in dry THF (260 mL) was added triethylamine·hydrofluoric acid complex (56 mL, 344 mmol) at ambient temperature. Reaction was stirred for 3 h. Reaction was diluted with ethyl acetate (350 mL) and washed with water (200 mL), brine (200 mL), dried (sodium sulfate), and evaporated to afford 21 (43 g, >100% crude yield). Reslurring of the crude compound in a mixture of hot ethyl acetate (350 mL) and hexanes (50 mL) gave pure 21 in 90% yield.

ESILRMS M+ calcd. For $C_{29}H_{36}O_{11}$: 560. Found 560.

6) Synthesis of baccatin derivative 22

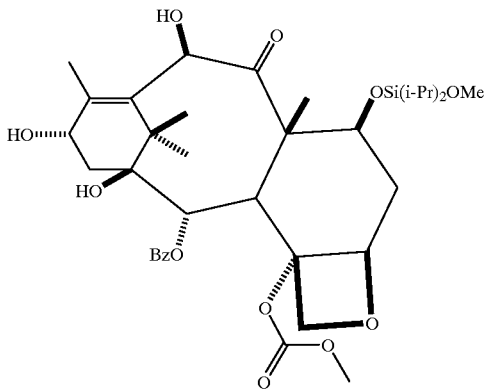

To a stirred solution of baccatin 21 (32 g, 57 mmol) and imidazole (11.7, 172 mmol in DMF (220 mL) at −65° C. was added diisopropyldichlorosilane (26.8 mL) under argon. Temperature of the reaction mixture was maintained at −60° C. and the mixture was stirred for 2 h. After completion of the reaction (HPLC), a solution of imidazole in methanol (11.7 g imidazole dissolved in 35 mL methanol) was added and the solution was stirred at 0° C. for 30 min. Mixture was extracted with TBME (500 mL). Organic phase was washed with water (4×150 mL), dried (sodium sulfate), and evaporated to afford crude 22 (45 g). The crude material was further dissolved in acetonitrile (150 mL) and the solution was washed with hexanes (3×100 mL). Removal of acetonitrile afforded pure 22 as a white solid (34 g, 84% yield).

ESILRMS M+ calcd. For $C_{36}H_{52}O_{12}Si$: 704. Found 704.

7) Synthesis of baccatin derivative 23

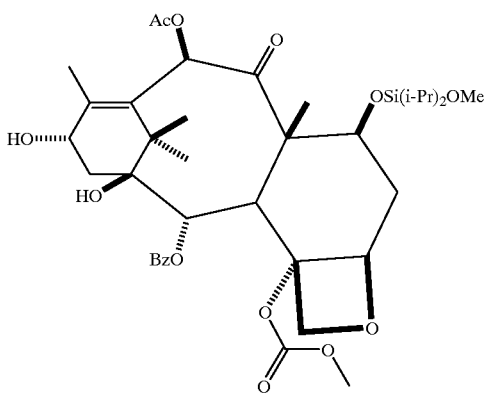

To a solution of baccatin derivative 22 (33.2 g, 47 mmol) in DMF (200 mL) was added LHMDS (61.2 mL, 61.2 mmol) dropwise at −43° C. Reaction was stirred for 15 min followed by the addition of acetic anhydride (5.8 mL, 63 mmol). Reaction was stirred for 30 min. at −40° C. Acetic acid (3.6 mL) was added and the cooling bath was removed. Reaction mixture was extracted with TBME (300 mL). Organic layer was separated and washed with water (3×150 mL), brine (150 mL), dried (sodium sulfate), and evaporated to afford the crude product. Purification of this compound was achieved by crystallization from a mixture of THF:heptane (1:6). Input of 40 g provided 21 g of crystallized baccatin derivative 23 (60% yield).

ESILRMS M+ calcd. For $C_{38}H_{54}O_{13}Si$: 746. Found 746.

8) Synthesis of paclitaxel derivative 25

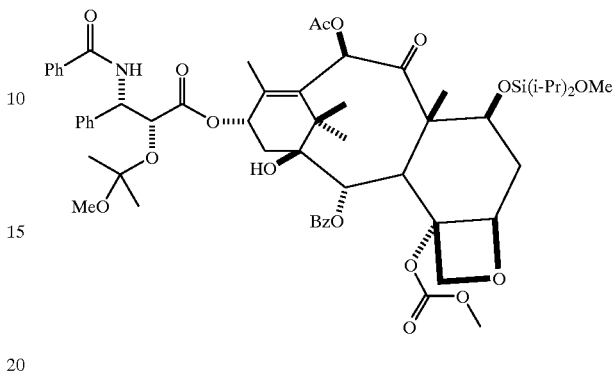

Under argon atmosphere, LHMDS (32 mL, 1 M solution in THF) was added to a stirred solution of baccatin derivative 24 (19 g, 25.5 mmol) in THF (65 mL) at −55° C. After stirring the solution for 10 min at −37° C., solution of β-lactam 24 (10.4 g, 30.6 mmol) in THF (25 mL) was added to the reaction mixture. Reaction mixture was warmed to 0° C. and stirred for 60 min. After completion of the reaction (as indicated by HPLC), pH 7 phosphate buffer (17 mL) was added followed by 20% solution of sodium bicarbonate (54 mL). Reaction mixture was extracted with ethyl acetate. The organic layer was washed with water, brine, and dried (anhydrous magnesium sulfate) to afford the crude coupled product. The compound was purified by crystallization (4:6 mixture of heptane/IPA) to provide 21.8 g of 25 (77%) of pure product.

ESILRMS M+ calcd. For $C_{57}H_{72}NO_{17}Si$: 1071. Found 1071.

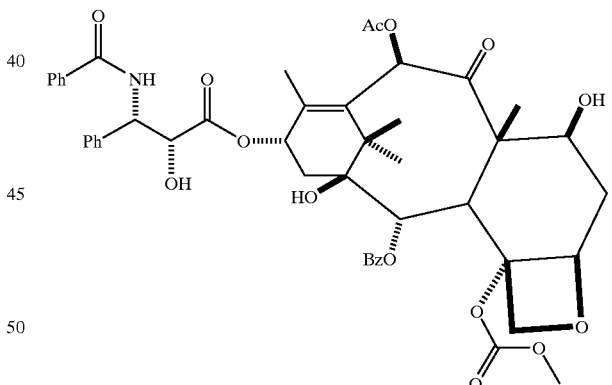

To a solution of paclitaxel derivative 25 in acetic acid (69 mL) was added a solution of trifluoroacetic acid in acetic acid (39 mL, 1 mmol solution prepared by dissolving 23.4 g of trifluoacetic acid in 120 mL of water and 69 mL of acetic acid) at ambient temperature. Reaction mixture was stirred for 17 h and quenched with 40% aqueous sodium acetate solution (6 equiv). Reaction was stirred for 20 min followed by the addition of dichloromethane (200 mL) and water (50 mL). The biphasic mixture was stirred for 20 min before separating the organic layer. Organic layer was washed with water (3×100 mL), dried (magnesium sulfate) and evaporated to afford 6.9 g of the crude product. Crystallization of the crude material from ethanol/heptane (1:1) gave 4.2 g (76%) of the title compound.

ESILRMS M+ calcd. For $C_{47}H_{51}NO_{15}$: 869. Found 869
Anal calcd. for $C_{47}H_{51}NO_{15}$: C, 64.89; H, 5.91; N, 1.61. Found: C, 64.79,; H, 5.82; N, 1.54.

Alternate coupling procedure via oxazole intermediate: Preparation of the paclitaxel derivative 27.

To a solution of baccatin derivative 23 (13.2 g, 17.6 mmol) in toluene (130 mL) was added 4-dimethylaminopyridine (3.24 g, 26 mmol), oxazole acid 26 (5.67 g, 21.2 mmol) and 1,3-dicyclohexylcabodiimide (DCC) (5.47 g, 26 mmol) at ambient temperature. Reaction mixture (slurry) was stirred for 3 h followed by the addition of acetic acid (2.1 mL) and stirring for additional 45 min. Mixture was diluted with ethyl acetate (200 mL) and washed with brine, 0.1 N hydrochloric acid, sodium bicarbonate, dried (magnesium sulfate), and evaporated to afford the crude 27. Purification was achieved by crystallization from 25% aqueous isopropanol; input of 18 g provided 15.8 g of pure product (86% yield).

ESILRMS M+ calcd. For $C_{54}H_{65}NO_{15}Si$: 996. Found 996.

Conversion of 27 to compound I:

To a solution of oxazole compound 27 (14.4 g 14.4 mmol) in acetic acid (123 mL) was added a solution of trifluoracetic acid in acetic acid (7.2 mL of trifluoroacetic acid in 29 mL of acetic acid) and water (28 mL) at ambient temperature. Reaction mixture was stirred for 18 h followed by the addition of sodium acetate (8.3 g) and water (30 mL). Solution was stirred for 5 min before adding dichloromethane (140 mL) and water (95 mL). Organic layer was separated, washed with water (150 mL) and transferred in the flask. To the stirred solution triethylamine (25 mL) was added while keeping the internal temperature of the reaction between 20–25° C. Reaction mixture was stirred for 45 min. Sulfuric acid (21 mL) and water (209 mL) was added and the organic layer was separated and washed with water, brine, dried (magnesium sulfate), and evaporated to afford 12.2 g of the title compound (97% yield). Purification was achieved by crystallization as mentioned earlier.

What is claimed is:

1. A process for the synthesis of a C-4 methylcarbonate analog of paclitaxel from 10-deacetylbaccatin, which comprises the steps of:

(a) preparing a C-4 methylcarbonate analog of 10-deacetylbaccatin from 10-deacetylbaccatin by reductive removal of the C-4 acetate using a reducing agent followed by the addition of a methylcarbonate to the C-4 hydroxyl group;

(b) selectively protecting the C-7 hydroxyl group with a dialkyldialkyloxysilane protecting group;

(c) acetylating the C-10 hydroxyl group;

(d) coupling a paclitaxel sidechain to the C-13 hydyroxyl group; and (e) deprotecting said silylether protecting group at C-7.

2. The process according to claim 1, wherein said preparing step (a) comprises the steps of:

(i) protecting the C-1, C-7, C-10 and C-13 hydroxyl groups of 10-deacetylbaccatin with a dialkyldialkyloxysilane protecting group;

(ii) protecting the C-1 hydroxyl group with a dialkylchlorosilyl protecting group as a dimethylsilyl ether;

(III) chemoselectively reducing the C-4 acetate group with said reducing agent;

(iv) adding a methylcarbonate group to the C-4 hydroxyl group; and (v) deprotecting the C-1, C-7, C-10 and C-13 protected hydroxyl groups to form C-4 methylcarbonate-10-deacetylbaccatin having the formula:

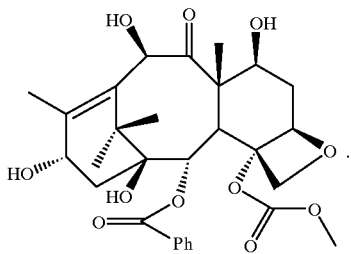

3. The process according to claim 2, wherein said reducing agent is Red-Al.

4. The process according to claim 3, wherein said dialkyldichlorosilane protecting group is diisopropylsilyidichloride.

* * * * *